United States Patent [19]

Mohrbacher et al.

[11] 4,196,300

[45] Apr. 1, 1980

[54] α-ALKYL-SUBSTITUTED GLYCIDATES AND THIOGLYCIDATES

[75] Inventors: Richard J. Mohrbacher, Maple Glen; Winston Ho, Hatfield; Gene Tutwiler, Churchville, all of Pa.

[73] Assignee: McNeilabs, Inc., Fort Washington, Pa.

[21] Appl. No.: 934,911

[22] Filed: Aug. 18, 1978

Related U.S. Application Data

[63] Continuation-in-part of Ser. No. 770,970, Feb. 22, 1977, abandoned, which is a continuation-in-part of Ser. No. 615,628, Sep. 22, 1975, abandoned.

[51] Int. Cl.$^2$ .................. C07D 331/02; C07D 303/40
[52] U.S. Cl. ..................................... 549/90; 424/275; 424/278; 260/544 L; 560/153; 560/205; 560/226; 562/556; 562/598; 260/348.46; 260/348.61
[58] Field of Search ........... 260/327 E, 348.46, 348.61

[56] References Cited
PUBLICATIONS

Morris et al., J. Am. Chem. Soc., vol. 77, pp. 1692–1693 (1955).
Zvonkova et al., Ch. Org. Khim. 1974, 10 (8), pp. 1621–1626, (cited as Chem. Abst., vol. 81, 151450v, 1974).
Zvonkova et al., Izv. Vyssh. Uchebn. Zaved. Khim, Khim. Tekhnol. 1976, 19(5), pp. 796–798, (cited as Chem. Abst., vol. 85, abst. 78038t (1976).
Omura et al., Antimicrob. Agents Chemother. 1974, 6(2), pp. 209–215, cited as Chem. Abst., vol. 82, abst. 52077t (1975).
Zawisza, Pol. J. Pharmacol. Pharm. 1974, 26(4), pp. 455–464, cited as Chem. Abstracts, vol. 82, abst. 98165y (1975).
Lowy et al., An Introduction to Organic Chemistry, 6th Ed., pp. 213 to 214, John Wiley and Sons, Inc. NY (1945).

*Primary Examiner*—John D. Randolph

[57] ABSTRACT

Glycidates and thioglycidates substituted in the α-position with a long chain alkyl of from 11 to 16 carbons having hypoglycemic activity.

25 Claims, No Drawings

α-ALKYL-SUBSTITUTED GLYCIDATES AND THIOGLYCIDATES

CROSS-REFERENCE TO RELATED APPLICATION

This is a continuation-in-part of our copending application Ser. No. 770,970, filed Feb. 22, 1977, now abandoned, which in turn was a continuation-in-part of application Ser. No. 615,628, filed Sept. 22, 1975, now abandoned.

DESCRIPTION OF THE INVENTION

The invention relates to novel α-alkyl glycidic and thioglycidic acid derivatives having the formula:

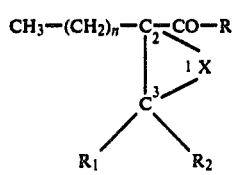

wherein n is an integer from 10 to 15, preferably wherein n is from 11 to 15 and most preferably from 11 to 13; R is a member selected from the group consisting of OH, O-loweralkyl, $NH_2$, NH-loweralkyl, NH-loweralkyl-OH and N(loweralkyl)$_2$; X is a member selected from the group consisting of O and S, preferably O; and $R_1$ and $R_2$ are each a member selected from the group consisting of hydrogen and loweralkyl; provided that, when said R is other than O-loweralkyl, then at least one of said $R_1$ and $R_2$ is hydrogen. The therapeutically acceptable basic salts of the foregoing acids, i.e., when R is OH, are also included within the scope of this invention. Among the preferred compounds are those wherein both $R_1$ and $R_2$ are hydrogen.

As used herein, the term "loweralkyl" may be straight or branch chained saturated hydrocarbons having from 1 to about 5 carbons, e.g., methyl, ethyl, propyl, isopropyl, sec-butyl, pentyl and the like alkyls.

The oxy esters of formula (I), wherein each of said $R_1$ and $R_2$ is hydrogen, are readily obtained from an appropriate α-alkylacrylic acid of formula (II). Such acids may be obtained according to the synthetic procedure described by Pfeffer et al., J. Org. Chem., 37, 1256 (1972). Conventional esterification of (II), with an appropriate loweralkanol esterifying agent yields the corresponding loweralkyl esters of formula (III). Epoxidation of (III) according to standard oxidation procedures with an appropriate organic percarboxylic acid as the oxidant affords the corresponding loweralkyl α-alkylglycidates of formula (IV). Typical epoxidation peracids include, for example, perbenzoic acid, haloperbenzoic acid, preferably m-chloroperbenzoic acid, monoperphthalic acid, peracetic acid and the like. Among the suitable solvents for the peroxidation reaction are, for example, a halogenated hydrocarbon, e.g., dichloroethane, chloroform and the like, and an ether, e.g., diethyl ether, dioxane and the like.

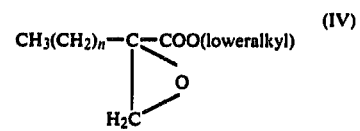

The oxy esters of formula (I), i.e., where X=O, wherein one of said $R_1$ and $R_2$ is loweralkyl, as shown in formula (VIII), may be prepared from the interaction of an appropriate loweralkyl β-loweralkylacrylate of formula (V), which has first been treated with a strong base capable of removing an α-hydrogen from said acrylate, with an appropriate alkyl halide of formula (VI), preferably the bromide or chloride. Typical of the utilizable strong bases are a lithium dialkylamide, e.g., LiN(i-Pr)$_2$, an alkali metal amide, e.g., NaNH$_2$, and the like. The reaction is conducted in a suitable aprotic inert organic solvent under an inert atmosphere, e.g., nitrogen, and preferably at low temperatures of −80° to −30° C. Suitable solvents include the loweralkanes such as hexane, heptane and the like and other solvents whose freezing points are low enough to be suitable for the cooled reaction conditions. A particularly useful solvent system is hexamethylphosphoramide (HMPA) as a cosolvent in tetrahydrofuran (THF). The thus-obtained esters (VII) may then be epoxidized, as previously described, to yield the desired oxy-esters of formula (VIII).

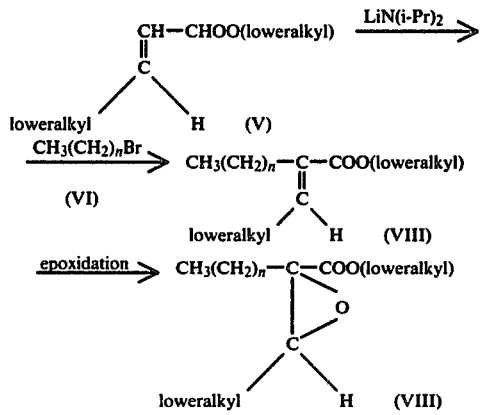

A general method for making all the oxy esters of formula (I), including those wherein both of said $R_1$ and $R_2$ are loweralkyl, is by the Darzens glycidic ester condensation type of reaction (see Newman in "Organic Reactions", Vol. 5, New York: John Wiley & Sons, Inc., 1949, Chap. 10). An aldol type condensation of an appropriate aldehyde or ketone with an appropriate α-halo ester produces the glycidic ester. Accordingly, an α-halo ester of formula (IX), pretreated with a suitable strong base, e.g., an alkali metal alkoxide or amide, capable of removing an α-hydrogen, is reacted with an appropriate aldehyde or ketone of formula (X) under Darzens reactions conditions to yield the desired oxy-esters (XI).

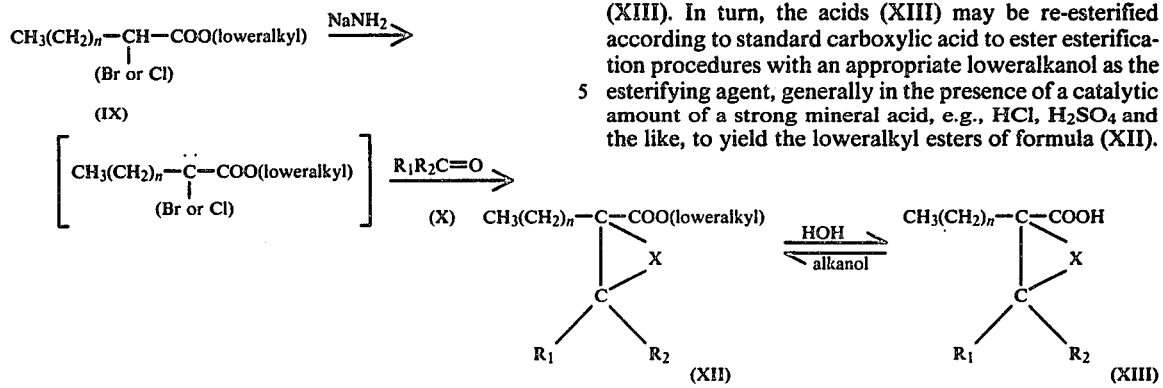

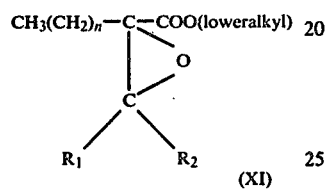

The thio esters of formula (I), i.e., with X=S, are obtained by transformation of the oxy function in (XI) to a thio function (XI-b) by treating (XI) with thiourea in the presence of a strong mineral acid, preferably sulfuric acid, in a suitable anhydrous organic solvent such as, for example, absolute methanol, ethanol and the like, and then neutralizing the thus-obtained intermediate of formula (XI-a) with an appropriate base, such as, for example, an alkali metal carbonate or bicarbonate.

The foregoing reactions may be illustrated by the following schematic diagram:

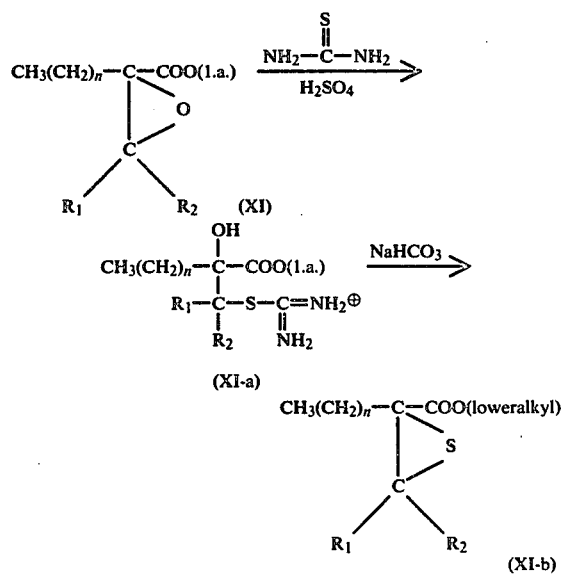

The oxy esters (XI) and the thio esters (XI-b) as shown in combined formula (XII) wherein X represents O or S, respectively, may then be used as precursors for making other respective oxy and thio derivatives of formula (I). For example, standard ester-to-acid hydrolysis of (XII) under conventional acidic of alkaline conditions affords the corresponding acids of formula (XIII). In turn, the acids (XIII) may be re-esterified according to standard carboxylic acid to ester esterification procedures with an appropriate loweralkanol as the esterifying agent, generally in the presence of a catalytic amount of a strong mineral acid, e.g., HCl, $H_2SO_4$ and the like, to yield the loweralkyl esters of formula (XII).

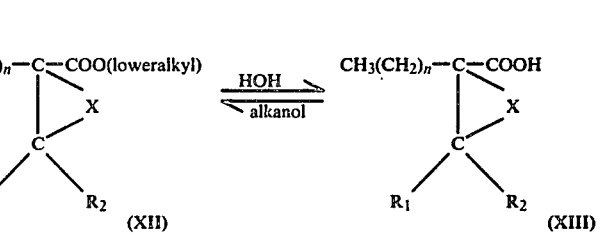

The acids of formula (XIII) may be converted to the corresponding salt form by treatment with a slight excess of an equivalent amount of an appropriate base, for example, an alkali metal or alkaline earth metal hydroxide, e.g., sodium hydroxide, potassium hydroxide, calcium hydroxide and the like, or with an organic amine base, e.g., mono-, di- and tri-loweralkyl amines such as ethylamine, propylamine, methylethylamine, triethylamine and the like, or other amines such as benzylamine, methylphenylamine, piperidine, pyrrolidine and the like.

The acids (XIII) may also be used as precursors for making the esters, amides and substituted amides of formula (I). For example, standard esterification procedures with an appropriate loweralkanol as the esterifying agent afford the corresponding loweralkyl esters (XII). The corresponding amides are obtained by standard acid-to-amide procedures, preferably by first transforming the carboxylic function of the acid (XIII) into the corresponding acid chloride form (XVII), for example, by treatment of the acid or its alkali metal salt with thionyl chloride or oxalyl chloride in an inert organic solvent suitable for such transformations, e.g., an aromatic hydrocarbon, chloroform and the like, and then reacting the thus-obtained acid chloride with either ammonia, loweralkyl amine or diloweralkyl amine in a suitable organic solvent for such ammonolysis reactions, e.g., an aromatic hydrocarbon, acetonitrile and the like, to yield the respective amides of formulas (XIV), (XV) and (XVI).

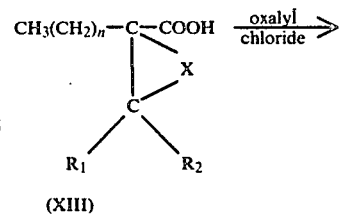

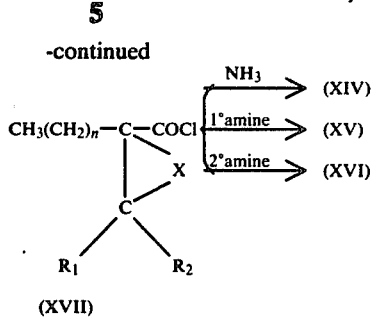

Alternatively, the amides of formula (I), wherein each of said $R_1$ and $R_2$ is hydrogen, may be prepared from the α-alkylacrylic acids of formula (II) by similar transformation to the corresponding acid chloride form (XVIII) followed by appropriate interaction with ammonia, primary or secondary amines to yield the respective α-alkylacrylic amides (XIX). Such amides are then epoxidized to the corresponding oxy amides (XX) which in turn may be converted to the corresponding thio amides (XXI) according to the relevant reaction techniques previously described for making the oxy esters and thio esters of formula (I). The foregoing reactions may be illustrated by the following schematic diagram in which the preparation of unsubstituted amides is exemplified.

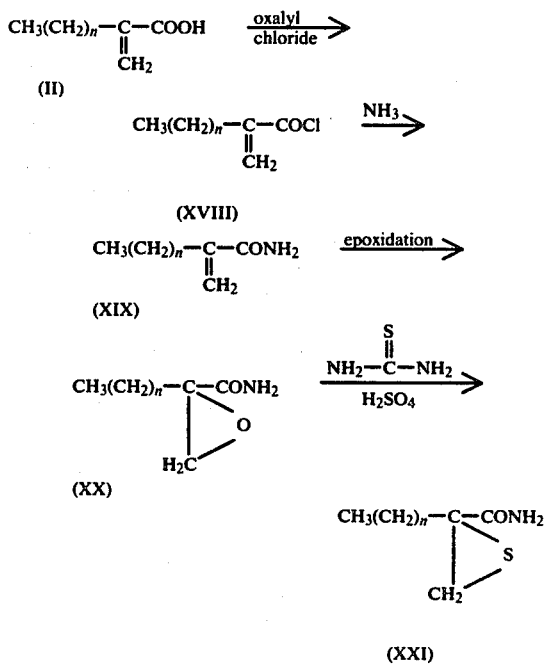

The oxo-amides and thio-amides of formula (I) may also be conveniently prepared from the acids (XIII) as follows. The acid is first transformed into an appropriate ammonium salt by standard treatment with a tertiary amine, as exemplified by the triethylammonium salt of formula (XXII). The salt is in turn transformed into a mixed anhydride (XXIII) by reaction with an appropriate haloalkylformate, preferably ethyl chloroformate, which anhydride is then reacted with ammonia or an appropriate primary or secondary alkylamine in a suitable inert aprotic organic solvent, for example, an ether, e.g., dioxane, tetrahydrofuran, and the like, or an aromatic hydrocarbon, e.g., benzene, toluene, xylene and the like to yield the respective amides of formula (XIV), (XV) and (XVI). Reaction of the anhydride with an appropriate alkanolamine in such aprotic solvent yields the compounds of formula (I) wherein R is NH-loweralkyl-OH.

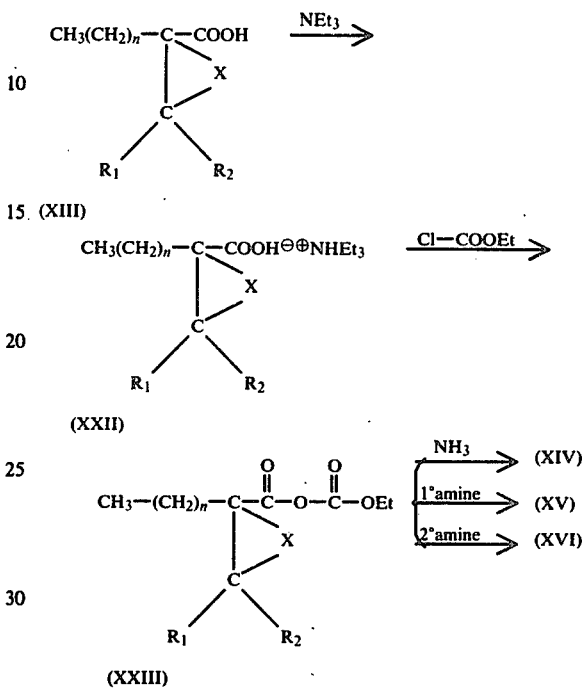

The compounds of formula (I) and salts thereof are useful for their hypoglycemic activity as demonstrated in a standard blood glucose tolerance test (GTT) in rats. Three to five glucose primed, fasted (18–24 hrs.), intact male rats are used for each test and control group. The compound to be tested is suspended in 0.5% aqueous methylcellulose and administered at doses of 10–150 mg/kg either intraperitoneally, subcutaneously or orally 30–60 minutes prior to administration of glucose. The glucose is given either orally (1 g/kg) or subcutaneously (0.8 g/kg). Serial blood samples are obtained from the tail without anesthesia at thirty minute intervals for 3 hours after administration of the glucose. Blood specimens are immediately deproteinized with barium hydroxide and zinc sulfate according to conventional GTT procedures and glucose levels are determined using the standard glucose oxidase assay. A significant depression of blood sugar from that of controls is observed with the subject compounds.

The following examples are intended to illustrate, but not to limit, the scope of the present invention.

EXAMPLE I

This example illustrates the method described by Pfeffer et al., J. Org. Chem., 37, 1256 (1972), for preparing α-alkylhydracrylic acids of the formula: $CH_3(CH_2)_n$—$C(CH_2OH)H$—COOH, wherein n is an integer from 10 to 14. These α-alkylhydracrylic acids are precursors for making the α-alkylacrylic acids of formula (II).

α-Hydroxymethylpalmitic acid

Anhydrous tetrahydofuran (THF) (825 ml) and 49.5 g (0.49 mole) of diisopropylamine were added to a dry three neck flask purged with nitrogen and maintained under a nitrogen atmosphere. After cooling the mixture to −20°, 300 ml of n-butyllithium in hexane (1.6 M) (0.49 mole) was added slowly to prevent the temperature from exceeding 0° and then 79.3 ml of anhydrous hexamethylphosphoramide (HMPA) (0.44 mole) was added. A solution of 51.28 g of palmitic acid (0.198 mole) in 400 ml of THF was added dropwise with stirring while maintaining the reaction temperature below 0°. A milky white suspension resulted after the addition of palmitic acid. The reaction mixture was brought to about 40° by using a warm water bath. The suspension changed to a clear solution as the temperature gradually reached 40°. This system was then connected to a formaldehyde generating system. Paraformaldehyde (40 g) was heated in a three neck flask at 180°–200° to generate formaldehyde and the formaldehyde vapors were carried by a stream of nitrogen over the surface of the stirred solution of α-lithiated lithium palmitate prepared previously. The reaction was terminated after complete depolymerization of paraformaldehyde (2 to 2½ hrs.). The reaction solution was cooled in an ice bath and neutralized with hydrochloric acid until acidic. The organic layer was separated and was concentrated under reduced pressure on a rotavac to remove most of the THF solvent. The resulting oily residue was dissolved in 2 liters of ether and was washed three times with 10% hydrochloric acid solution and then twice with water. The ether layer was dried over $Na_2SO_4$ and the solvents were removed under reduced pressure to give 43.3 g (75%) of crude product, α-hydroxymethylpalmitic acid, which was recrystallized once from acetone to give 39.0 g (69% yield) of the product with m.p. 67°–71°, which was used without further purification in the next synthetic step.

EXAMPLE II

By repeating the procedure of Example I, except that an equivalent amount of an appropriate fatty acid is substituted for the palmitic acid used therein the following respective α-alkylhydracrylic acids are obtained:

| Fatty Acid | Product |
| --- | --- |
| tridecyclic | $CH_3(CH_2)_{10}C(CH_2OH)HCOOH$ |
| myristic | $CH_3(CH_2)_{11}C(CH_2OH)HCOOH$ |
| pentadecylic | $CH_3(CH_2)_{12}C(CH_2OH)HCOOH$ |
| margaric | $CH_3(CH_2)_{14}C(CH_2OH)HCOOH$ |

EXAMPLE III

This example illustrates a method (see Pfeffer et al., ibid.) of preparing the α-alkylacrylic acids of formula (II) through dehydration of the appropriate α-alkylhydracrylic acid precursor.

A. 2-Tetradecylacrylic acid

A 34.25 g sample of α-hydroxymethylpalmitic acid (0.119 mole) and 17 drops of phosphoric acid (85%) were placed in a distillation flask and the mixture heated to 245°–255° C. in an oil bath under vacuum. The product, 2-tetradecylacrylic acid, distilled over at 155°–160° C. at 0.10 mm Hg (24.80 g; 77% yield) and was crystallized from acetone, m.p. 53°–55° C.

B. By repeating the foregoing procedure, except that an equivalent quantity of each of the α-alkylhydracrylic acids obtained in Example II is used as the starting material, the following respective products are obtained:

2-undecylacrylic acid;
2-dodecylacrylic acid;
2-tridecylacrylic acid; and;
2-pentadecylacrylic acid.

EXAMPLE IV

A. Methyl 2-tetradecylacrylate 14.6 Grams of 2-tetradecylacrylic acid (0.052 mole) are combined with 65 ml of absolute methanol and 15 ml of 51% $BF_3$ in methanol in a 200 ml flask equipped with a condenser and drying tube. The system is heated under reflux for six hours (two layers appear when cooled). The mixture is concentrated to ½ volume and the acid is neutralized with saturated $NaHCO_3$ solution to about pH 7. The oily material is extracted with ether, washed with water and dried over anhydrous $MgSO_4$. The ether solvent is removed under reduced pressure. The oily residue of methyl 2-tetradecylacrylate (14.70 g) is not purified further (>95% pure by GC) and used directly in the next step.

B. The foregoing esterification procedure is followed to prepare the loweralkyl α-alkylacrylates of formula (III). By substituting equivalent quantities of an appropriate α-alkylacrylic acid and an appropriate loweralkanol esterifying agent as starting materials, the following respective products are obtained:
butyl 2-undecylacrylate;
methyl 2-dodecylacrylate;
methyl 2-tridecylacrylate;
ethyl 2-tetradecylacrylate; and
isopropyl 2-pentadecylacrylate.

EXAMPLE V n-Butyl α-Tetradecyl acrylate 4.27 Grams (15.9 m mole) of tetradecyl acrylic acid is dissolved in 80 ml anhydrous n-butanol in a 300 ml one-neck round-bottom flask equipped with $CaCl_2$-drying tube, condenser, and magnetic stirrer. 24-ml of 98% $BF_3$ etherate is added and the solution refluxed for 6 hrs. The solution is then cooled to room temperature, neutralized with aqueous $NaHCO_3$ to pH 7 and extracted with ether. The ether solution is dried ($MgSO_4$) and evaporated giving 4.4 g (86% yield) of the product, n-butyl α-tetradecyl acrylate (about 93% pure) which is used without further purification in the next synthetic step.

EXAMPLE VI n-Butyl 2-tetradecyl glycidate 4.2 Grams (0.0131 mole) of n-butyl α-tetradecyl acrylate (93% pure) is combined with 113 ml dry dichloroethane, 0.0558 g of 3-t-butyl-4-hydroxy-5-methyl phenyl sulfide inhibitor, and 3.5 g (0.0201 mole) of m-chloroperbenzoic acid. The solution is refluxed for 3 hours and then chilled and filtered. The filtrate is successively concentrated to about ½ volume, re-filtered, washed with saturated aqueous $K_2CO_3$ and extracted with ether. The ether extract is dried over anhydrous $MgSO_4$ and evaporated in vacuo, and the product recrystallized from absolute methanol with cold filtration to give about 1.8 g of the product, n-butyl 2-tetradecyl glycidate.

EXAMPLE VII

Methyl 2-tetradecylglycidate

A mixture of 8.9 g (0.0316 mole) of methyl α-tetradecylacrylate, 10.9 g (0.0632 mole) of m-chloroperbenzoic acid and 0.205 g (0.000572 mole) of 3-t-butyl-4- hydroxy-5-methylphenyl sulfide inhibitor in 300 ml of dry 1,2-dichloroethane is stirred and refluxed for 4 hours. After an additional 18 hours stirring at room temperature the mixture is filtered and the filtrate concentrated in vacuo to ⅓ volume, cooled and refiltered. Ether is added to the filtrate which is then washed with $K_2CO_3$ solution and then with water. The ether layer is dried over anhydrous magnesium sulfate. After removal of the drying agent the ether solvent is evaporated in vacuo. The oily residue solidifies on cooling to give about 10.6 g of product, methyl 2-tetradecylglycidate which is recrystallized from methanol: white crystals, m.p. 43°–45° C.

EXAMPLE VIII

The epoxidation procedures of Examples VI and VII may be followed in preparing the oxo esters of formula (IV). For example by repeating the procedure of Example VII, except that an equivalent amount of an appropriate loweralkyl 2-alkylacrylate is employed as the material to be epoxidized, the following products are obtained:
butyl 2-undecylglycidate;
methyl 2-dodecylglycidate, m.p. 38°–42° C.;
methyl 2-tridecylglycidate, m.p. 38°–39° C.;
ethyl 2-tetradecylglycidate; and
isopropyl 2-pentadecylglycidate.

EXAMPLE IX

Methyl 2-tetradecylthioglycidate 1.27 grams (0.0167 mole) of thiourea and 5.00 ml of 95–98% $H_2SO_4$ are placed in a one-liter three-neck round-bottom flask equipped with a condenser, magnetic stirrer and addition funnel along with 400 ml of absolute methanol. Then 5.00 g (0.0167 mole) of methyl 2-tetradecylglycidate dissolved in 50 ml of absolute methanol is added and the mixture stirred at room temperature for 3 hours. 400 Ml more of absolute methanol is added and the mixture is neutralized by addition of $NaHCO_3$ (1.7 g) with stirring. When the pH rises above 7 an oily material is seen to come out of solution and at this point the neutralization is considered complete. The solvent is removed in vacuo and the residue partitioned between water and ether. The ethereal layer is washed twice with $H_2O$ and once with saturated NaCl solution, dried over anhydrous $Na_2SO_4$ and concentrated in vacuo to yield about 5.77 g of a light tan solid. Column chromatography is employed to isolate the pure material, methyl 2-tetradecylthioglycidate.

EXAMPLE X

By following the procedure of Example IX, the transformation of the oxo function in formula (IV) compounds to the thio function in formula (XI) compounds is accomplished. For example, by substituting an equivalent amount of each of the oxo esters obtained in Example VIII for the methyl 2-tetradecylglycidate used in Example IX, the following thioglycidates of formula (XI) are obtained:
butyl 2-undecylthioglycidate;
methyl 2-dodecylthioglycidate;
methyl 2-tridecylthioglycidate;
ethyl 2-tetradecylthioglycidate; and
isopropyl 2-pentadecylthioglyciate.

EXAMPLE XI

A. 2-Tetradecylglycidic Acid 3.6 Grams (12.2 m mole) of methyl 2-tetradecylglycidate is dissolved in minimal absolute ethanol (about 40 ml) and set aside. 10.8 Ml of absolute ethanol is placed in a 100 ml three-neck round-bottom flask equipped with magnetic stirrer, $CaCl_2$ drying tube, thermometer and addition funnel. The ethanol is chilled in an ice bath and 0.3 g of sodium metal is added. When formation of sodium ethoxide is completed, the ethanol solution of methyl 2-tetradecylglycidate is added dropwise. After addition is completed and stirred for 15 min., 0.24 g of water is added and the mixture is stirred (25° C.) overnight (about 15 hours). The resulting suspension is filtered (sintered funnel) and the precipitate washed with ether, dried and then combined with 75 ml 1 N HCl and stirred for 4 hours. The suspension is extracted into ether. The ether extract is dried over dried anhydrous $Na_2SO_4$ and evaporated in vacuo, giving quantitative conversion to the acid. Recrystallization from acetone gives about 2.5 g (74% yield) of the product, 2-tetradecylglycidic acid, m.p. 77°–79° C.

B. The ester-to-acid hydrolysis procedure of Example XI-A illustrates a method of making the 2-alkylglycidic acids of formula (XIII). For example, by utilizing therein an equivalent amount of each oxo-esters obtained from Example VIII, the corresponding oxo-acids of formula (XIII) are respectively obtained.

EXAMPLE XII

A. 2-Tetradecylthioglycidic Acid

A solution of 3.15 g (0.01 mole) of methyl 2-tetradecylthioglycidate in 50 ml of absolute ethanol is added dropwise to a cooled (0°–5° C.) solution of sodium ethoxide (0.25 g sodium in 12 ml absolute ethanol). The mixture is stirred for 15 minutes while maintaining the temperature below 20° C. and 0.19 g of water is added. Stirring is continued overnight (about 15 hours) at room temperature. The resulting suspension is filtered and the precipitate washed with ether, dried and then stirred for several hours in dilute HCl. The acidic suspension is extracted with ether and the ether layer dried ($Na_2SO_4$) and evaporated in vacuo giving the product, 2-tetradecylthioglycidic acid, in good yield.

B. The ester-to-acid hydrolysis procedure of Example XII-A illustrates a method for making the 2-alkylthioglycidic acid of formula (XIII). For example, by utilizing therein an equivalent amount of each thio-ester obtained from Example X, the corresponding thio-acids of formula (XIII) are respectively obtained.

EXAMPLE XIII

A. 2- Tetradecylacrylamide 5.4 Grams (0.02 mole) of 2-tetradecylacrylic acid is dissolved in 200 ml benzene and combined with 10.7 ml oxalyl chloride and stirred overnight (bubbling noted). The mixture is evaporated and the residue dissolved in benzene. The benzene solution is evaporated to dryness. This dissolution in and evaporation of benzene is repeated three times to ensure removal of unreacted oxalyl chloride and other noxious gaseous by-products. The residue containing 2-tetradecylacrylic acid chloride is combined with 100 ml benzene and 80 ml of 4.7% ammonia in acetonitrile. The mixture is stirred overnight and then filtered. Filtration gives about 4.5 g of solid material containing some $NH_4Cl$ as a by-product. The filtrate is washed with water, dried ($Na_2SO_4$) and evaporated to give about 1.6 g of oily residue (residue A). The 4.5 grams of filtered solid material is mixed with 100 ml of diethylether/chloroform (1:1) and the resultant solution is washed with water. The organic phase is then dried (Na₂SO₄) and evaporated to give about 3.1 g of oily residue (residue B). The two oily residues (A and B), containing the product, 2-tetradecylacrylamide, are combined and used in the next synthetic step (see Example XIV-A) without further purification.

B. The foregoing acid to acid chloride to acid amide synthesis illustrates an amidation procedure which can be used to prepare the α-alkylacrylic amides of formula (XIX). By repeating such procedure, except that an equivalent quantity of each α-alkylacrylic acid obtained from Example III-B is substituted for the 2-tetradecylacrylic acid utilized in Example XIII-A, there are obtained, as respective products, the corresponding 2-alkylacrylamides.

EXAMPLE XIV

A. 2-Tetradecylglycidamide 4.0 Grams of 2-methylene hexadecanoamide is combined with 145 ml dry 1,3-dichloroethane, 0.083 g of 3-t-butyl-4-hydroxy-5-methyl-phenyl sulfide inhibitor and 4.4 g of m-chloro perbenzoic acid (85%). The mixture is heated to reflux for 3 hrs. with stirring. The mixture is then cooled to room temperature and concentrated to about ⅓ volume. The decreased volume is filtered and the filtrate washed with saturated aqueous K₂CO₃ and extracted with chloroform. The chloroform extract is dried (M₉SO₄) evaporated and the crude product recrystallized from absolute methanol to give about 1.1 g of 2-tetradecylglycidamide, m.p. 104°–106° C.

B. The epoxidation procedure of Example XIV-A is repeated, except that an equivalent quantity of each 2-alkylacrylamide obtained in Example XIII-B is substituted as the starting material to be epoxidized, to yield the following respective oxy-amides of formula (XX):
2-undecylglycidamide;
2-dodecylglycidamide;
2-tridecylglycidamide; and
2-pentadecylglycidamide.

EXAMPLE XV

The procedure described in Example X for the transformation of oxo-esters to thio-esters is followed to also transform the oxo-amides of formula (XX) to thioamides of formula (XXI). Accordingly, substitution of an equivalent amount of each of the oxo-amides obtained in Examples XIV-A and B for the methyl 2-tetradecylglycidate used in Example IX affords the corresponding 2-alkylthioglycidamides of formula (XXI) as respective products.

EXAMPLE XVI

A. Methyl 2-tetradecylcrotonate

To a solution of distilled di-isopropylamine (5.06 g; 0.05 mole) in 50 ml anhydrous THF maintained at −78° C. is added dropwise 36 ml of n-butyllithium in hexane (1.39 M; 0.05 mole) under a nitrogen atmosphere, followed by dropwise addition of anhydrous HMPA (9.86 g; 0.055 mole). The mixture is maintained at −78° C. for about one-half hour and then methyl crotonate (5 g; 0.05 mole) is added dropwise. Ten minutes following complete addition of the methyl crotonate, 15.3 g of myristyl bromide (0.055 mole) is added. The system is then allowed to warm to ≦ −30° C. and is maintained at this temperature for about 1 hour with stirring. The system is then allowed to reach ambient temperature with continued stirring overnight (about 15 hours). The system is worked-up to pH5 with 1 N HCl and then extracted with ether. The ether extract is washed successively with water and saturated brine, then dried over anhydrous Na₂SO₄ and evaporated in vacuo. The crude oily product is purified by column chromatography (silica gel):

| Fraction No. | Eluting Solvent | Volume of Solvent |
|---|---|---|
| 1–5 | 100% pet ether | 1000 ml |
| 6–13 | 10% benzene in pet ether | 1000 ml |
| 14–22 | 25% benzene in pet ether | 1000 ml |

Fraction Nos. 20–22 are combined and the product, methyl 2-tetradecylcrotonate, is obtained in 98.4% purity by standard isolation techniques.

B. The procedure of Example XVI-A illustrates a method of preparing the unsaturated esters of formula (VII). By following such procedure, except that an equivalent amount of the appropriate precursors are utilized, the following products are obtained:

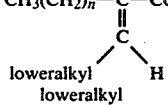

| | —COO(l.a.) |
|---|---|
| Me | —COOEt |
| n-Pr | —COOMe |
| n-Bu | —COOPr |
| Me | —COOMe |

EXAMPLE XVII

A. Methyl 2-tetradecyl-3-methylglycidate 1.09 Grams (3.7 mmole) of methyl 2-tetradecylcrotonate is combined with 62 ml dry 1,2-dichloroethane, 0.037 g (0.103 mmole) of 3-t-butyl-4-hydroxy-5-methylphenyl sulfide inhibitor and 1.3 g (7.4 mmole) of m-chloroperbenzoic acid. The mixture is refluxed for 4 hours. After the additional 18 hours stirring at room temperature, the mixture is filtered and the filtrate concentrated in vacuo to ⅓ volume, cooled and refiltered. Ether is added to the filtrate which is then extracted with K₂CO₃ solution and then with water. The ether layer is dried over anhydrous MgSO₄. After removal of the drying agent, the ether solvent is evaporated in vacuo. The oily residue is purified by column chromatography (silica gel):

| Fraction No. | Eluting Solvent | Volume of Solvent |
|---|---|---|
| 1 | 100% pet ether | 50 ml |
| 2–10 | 10% Et₂O in pet ether | 200 ml |
| 11 | 25% Et₂O in pet ether | 100 ml |

Fractions 7–9 are combined and the product, methyl 2-tetradecyl-3-methylglycidate, is obtained by standard isolation techniques.

B. The epoxidation procedure of Example XVII-A is repeated, except that an equivalent amount of each of the unsaturated esters obtained in Example XVI-B are utilized as the starting material to be epoxidized to yield, as respective products, the corresponding 3-substituted oxo esters of formula (VIII).

C. By following the procedure of Example IX, except that an equivalent amount of the 3-substituted oxo esters obtained from Examples XVII-A and B are utilized as the starting material, transformation of the oxo function to a thio function is accomplished to give the corresponding 3-substituted thio esters of formula (XI-b).

D. The ester to acid hydrolysis procedures of Examples XI and XII are followed to prepare the corresponding 3-substituted oxo and thio acids of formula (XIII) by starting with an equivalent amount of each of the 3-substituted esters obtained heretofore in this example.

EXAMPLE XVIII

A. N-Ethyl-2-tetradecylthioglycidamide

To a stirred solution of 0.3 g (0.001 mole) of 2-tetradecylthioglycidic acid in 10 ml of anhydrous tetrahydrofuran (THF) at 0° C. (ice-water bath) is added 1.01 g (0.001 mole) of triethylamine in a small amount of THF. The mixture is stirred at 0° C. for about 30 minutes. To the thus-formed triethylammonium 2-tetradecylthioglycidate is added 0.108 g (0.001 mole) of ethyl chloroformate in small amount of THF and the mixture is stirred at about 0° C. (ice-water bath) for about 3 hours to prepare the corresponding mixed anhydride (a ppt. of Et$_3$NHCl is observed). A stoichiometric excess of ethylamine in THF is then added and the mixture stirred at room temperature for 16 hours. The THF solvent is concentrated to approximately ¼ volume, water is added and the mixture extracted with ether. After drying the ether extract (Na$_2$SO$_4$), the solvent is removed in vacuo giving the desired product, N-ethyl-2-tetradecylthioglycidamide, in good yield.

B. By repeating the acid to amide procedure of Example XVI-A, except that an equivalent amount of an appropriate 2-alkylglycidic acid or 2-alkylthioglycidic acid and an appropriate primary or secondary amine are employed as precursors, the following respective products are obtained:
N-methyl-2-tetradecylglycidamide;
N,N-dimethyl-2-dodecylthioglycidamide;
N-methyl-N-ethyl-2-tridecylglycidamide;
N-(n-butyl)-2-tridecylglycidamide
N,N-diethyl-2-pentadecylthioglycidamide;
N-ethyl-2-tetradecyl-3-methylglycidamide; and
N,N-diethyl-2-tetradecyl-3-methylthioglycidamide.

EXAMPLE XIX

This example demonstrates a Darzens glycidic ester synthesis for making the oxo esters of formula (I).

A. Methyl 2-Tetradecyl-3,3-dimethylglycidate

To a solution of 2.068 g of methyl bromopalmitate (0.0059 mole) in 0.343 g of acetone at 10°–15° C. with stirring is slowly added 5.57 ml of potassium t-butoxide solution (prepared from 0.58 g potassium and 16.5 ml t-butanol). The reaction mixture is stirred at room temperature for about one hour. Ether is added and the ether layer is separated and washed successively with dilute HCl, water and saturated brine. The ether layer is then dried over anhydrous MgSO$_4$ and the solvent evaporated off leaving an oily residue (about 1.84 g crude) which is purified by chromatography over silica gel in pet-ether (wetpacked; using 5% ether in pet-ether as eluting solution) to give the product, methyl 2-tetradecyl-3,3-dimethyl-glycidate in about 38% yield; m.p. 39°–40° C.

B. By following the procedure of Example XIX-A, except that an equivalent quantity of an appropriate aldehyde or ketone is used in place of the acetone used therein, the following respective products are obtained:
methyl 2-tetradecylglycidate;
methyl 2-tetradecyl-3-methylglycidate;
methyl 2-tetradecyl-3-methyl-3-ethylglycidate; and
methyl 2-tetradecyl-3,3-diethylglycidate.

EXAMPLE XX

Transformation of the oxy function in each of the oxy esters obtained in Example XIX to a thio function according to the relevant procedures previously described yields the following thioglycidates of formula (I):
methyl 2-tetradecyl-3,3-dimethylthioglycidate;
methyl 2-tetradecylthioglycidate;
methyl 2-tetradecyl-3-methylthioglycidate;
methyl 2-tetradecyl-3-methyl-3-ethylthioglycidate; and
methyl 2-tetradecyl-3,3-diethylthioglycidate.

EXAMPLE XXI

A. Hydrolysis of the ester function in each appropriate oxy ester obtained in Example XIX and in each appropriate thio ester obtained in Example XX according to the relevant procedures previously described affords the following corresponding acids of formula (I):
2-tetradecyl-3-methylglycidic acid;
2-tetradecylthioglycidic acid; and
2-tetradecyl-3-methylglycidic acid.

B. By following the applicable acid-to-amide procedures described in Examples XIV and XV, each of the foregoing acids are converted into the corresponding amides of formula (I).

EXAMPLE XXII

N,N-Dimethyl-2-tetradecylglycidaminde

To a solution of 1.42 g (0.005 mole) of 2-tetradecylglycidic acid in 10 ml of tetrahydrofuran (THF) at 0° C. (ice-water bath) with stirring is added 0.50 g (0.005 mole) of triethylamine in a small amount of THF. The solution is stirred at 0° C. for 30 minutes and 0.51 g (0.005 mole) of ethyl chloroformate is added. The mixture is stirred at about 0° C. (ice-water bath) for 3 hours (ppt. of Et$_3$N.HCl observed). At the end of 3 hours 0.429 g (0.015 mole) of dimethyl amine in THF is added and the mixture stirred overnight (16 hours) at room temperature. The THF solvent is concentrated to about ⅛ its volume, water is added and the mixture extracted with ether. The ether extract is dried over Na$_2$SO$_4$ and the ether solvent removed. A crude oily residue is obtained which is purified by column chromatography on silica gel. A 37.8% yield of pure N,N-dimethyl-2-tetradecylglycidamide is obtained, m.p. 40°–42° C.

EXAMPLE XXIII

N-(2-Hydroxyethyl)-2-tetradecylglycidamide

To a solution of 0.2 g of 2-tetradecylglycidic acid (0.0007 mole) in 10 ml of anhydrous THF at 0° C. (ice-water bath) with stirring is added 0.070 g of triethylamine (0.0007 mole) in a small amount of THF. The solution is stirred at 0° for 30 minutes and 76 mg. of ethyl chloroformate (0.0007 mole) in a small amount of THF is added. The mixture is stirred at about 0° C. (ice-water bath) for 3 hours (ppt. of Et$_3$NHCl observed). At the end of 3 hours 0.042 g. (0.0007 mole) of ethanolamine in THF is added. The mixture is stirred at room temperature for 16 hours. The THF solvent is concentrated to about ⅛ its volume, water is added and the mixture extracted with ether. The ether extract is dried over Na$_2$SO$_4$ and the ether solvent removed to give a white solid of N-(2-hydroxyethyl)-2-tetradecylglycidamide which, upon recrystallization from acetone has a m.p. of 80°-82° C.

EXAMPLE XXIV

By repeating the procedure of Example XXIII, except that an equivalent quantity of an appropriate 2-alkylglycidic acid or 2-alkylthioglycidic acid and an appropriate alkanolamine are employed as precursors, the following respective products are obtained:
N-(2-hydroxyethyl)-2-tridecylglycidamide;
N-(2-hydroxyethyl)-2-pentadecylglycidamide;
N-(3-hydroxypropyl)-2-tetradecylglycidamide;
N-(2-hydroxyethyl)-2-dodecylthioglycidamide;
N-(2-hydroxyethyl)-2-tetradecylthioglycidamide; and
N-(3-hydroxypropyl)-2-pentadecylglycidamide.

EXAMPLE XXV

α-Hydroxymethylstearic Acid

Anhydrous THF (327 ml) and 19.7 g (0.195 mole) of diisopropylamine are added to a dry three-neck flask purged with nitrogen and maintained under a nitrogen atmosphere. After cooling the mixture to −20° C., 123 ml of n-butyllithium in hexane (1.6 M) (0.195 mole) is added slowly to prevent the temperature from exceeding 0° C. and then 32.2 ml of anhydrous HMPA (0.18 mole) is added. A solution of 23.0 g of stearic acid (0.081 mole) in 165 ml of THF is added dropwise with stirring while maintaining the reaction temperature below 0° C. A milky white suspension results after the addition of stearic acid. The reaction mixture is brought to about 40° C. by using a warm water bath. The suspension changed to a clear solution as the temperature gradually reaches 40° C. This system is then connected to a formaldehyde generating system. Paraformaldehyde (16.4 g) is heated in a three-neck flask at 180°-200° C. to generate formaldehyde and the formaldehyde vapors are carried by a stream of nitrogen over the surface of the stirred solution of α-lithiated lithium stearate prepared previously. The reaction is terminated after complete depolymerization of paraformaldehyde (2 to 2½ hrs.). The reaction solution is cooled in an ice bath and neutralized with hydrochloric acid until acidic. The organic layer is separated and then concentrated under reduced pressure to remove most of the THF solvent. The resulting oily residue is dissolved in 2 liters of ether and washed three times with 10% hydrochloric acid and then twice with water. The ether layer is dried over Na$_2$SO$_4$ and the solvents removed under reduced pressure to give 22.4 g (92%) of crude product which is recrystallized once from acetone to give 17.3 g (71% yield) of α-hydroxymethylstearic acid, m.p. 62°-67° C. This material is used for the next reaction withouth further purification.

EXAMPLE XXVI

2-Hexadecyl acrylic acid

A 16.3 g sample of α-hydroxymethylstearic acid (0.0542 mole) and 6 drops of phosphoric acid (85%) are placed in a distillation flask and the mixture heated to 245°-255° C. in an oil bath under vacuum. The product, 2-hexadecyl acrylic acid, which distills over at 165°-175° C. at 0.1 mm (7.0 g) (43%), is recrystallized from acetone, m.p. 59°-63° C.

EXAMPLE XXVII

Methyl-2-hexadecyl acrylate

2-Tetradecylacrylic acid (6.5 g, 0.219 mole) is added with 27 ml of absolute methanol to a 50 ml round-bottom flask equipped with a magnetic stirrer and a condenser. Then 6.6 ml of 51% BF$_3$ in methanol is added and the soluion refluxed for 6 hours during which 2 layers appear. The mixture is concentrated to ½ original volume giving an emulsion which is brought to pH=6 with saturated NaHCO$_3$. The mixture is then extracted 3×50 ml ether. The combined ethereal extracts are washed 2×50 ml H$_2$O and 2×50 saturated aqueous brine, passed through a cotton plug, dried (MgSO$_4$) and concentrated in vacuo giving 7.0 g of methyl-2-hexadecyl acrylate as a light, yellow oil.

EXAMPLE XXVIII

Methyl 2-hexadecylglycidate

A sample of methyl 2-hexadecylacrylate (6.8 g, 0.0279 mole) and 0.125 g of sulfide inhibitor are placed in a 500 ml round-bottom flask with a magnetic stirrer, condenser and drying tube along with 170 ml dry 1,2-dichloroethane. Then 10.05 g (0.0580 mole) of m-chloroperbenzoic acid are added in 170 ml of dry 1,2-dichloroethane and the resulting yellow solution is refluxed for 4 hours. The mixture is then cooled in an ice bath and the resulting crystals are filtered off. The mixture is washed with 5% NaHSO$_3$ until a negative test for peroxide (starch iodide paper) is obtained and then concentrated in vacuo to about ⅓ original volume. The resulting emulsion is then neutralized with saturated K$_2$CO$_3$ and partitioned between Et$_2$O and H$_2$O. The ethereal extract is washed 2×100 ml water, 2×75 ml saturated brine, dried (MgSO$_4$) and concentrated in vacuo to yield 6.9 g (96%) of a light yellow solid. This material is recrystallized from methanol to yield 3.97 g of a white crystalline solid (56%), methyl 2-hexadecylglycidate, m.p. 40°-41° C.

EXAMPLE XXXIX

A. By following the hydrolysis procedure of Example XI, except that an equivalent amount of methyl 2-hexadecylglycidate is employed as the starting material to be hydrolyzed, there is obtained as the product the corresponding acid, 2-hexadecylglycidic acid.

B. The acid to amide procedure of Example XXII is repeated using an equivalent amount of 2-hexadecylglycidic acid as the starting material to yield as the product, N,N-dimethyl-2-hexadecylglycidamide.

What is claimed is:

1. A compound selected from the group consisting of glycidic and thioglycidic acid derivatives having the formula:

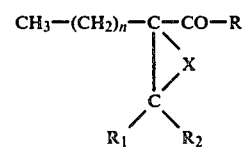

wherein n is an integer from 10 to 15; R is a member selected from the group consisting of OH, O-loweralkyl, NH$_2$, NH-loweralkyl, NH-loweralkyl-OH and N(loweralkyl)$_2$; X is a member selected from the group consisting of O and S; and each of R$_1$ and R$_2$ is a member selected from the group consisting of hydrogen and loweralkyl; provided that, when said R is other than O-lower-alkyl, then at least one of said $R_1$ and $R_2$ is hydrogen; and the therapeutically active basic salts of the foregoing acids.

2. The compounds of claim 1 wherein said n is an integer from 11 to 13.

3. A compound selected from the group consisting of glycidic acid derivatives having the formula:

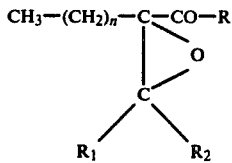

wherein n is an integer from 10 to 15; R is a member selected from the group consisting of OH, O-loweralkyl, $NH_2$, NH-loweralkyl, NH-loweralkyl-OH and N(loweralkyl)$_2$; and each $R_1$ and $R_2$ is a member selected from the group consisting of hydrogen and loweralkyl; provided that when said R is other than O-loweralkyl, then at least one of said $R_1$ and $R_2$ is hydrogen; and the therapeutically active basic salts of the foregoing acids.

4. The compounds of claim 3 wherein said n is an integer from 11 to 13.

5. A compound selected from the group consisting of thioglycidic acid derivatives having the formula:

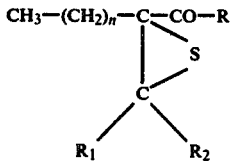

wherein n is an integer from 10 to 15; R is a member selected from the group consisting of OH, O-loweralkyl, NH-loweralkyl, NH-loweralkyl-OH and N(loweralkyl)$_2$; and each of $R_1$ and $R_2$ is a member selected from the group consisting of hydrogen and loweralkyl; provided that when said R is other than O-loweralkyl, then at least one of said $R_1$ and $R_2$ is hydrogen; and the therapeutically active basic salts of the foregoing acids.

6. The compounds of claim 5 wherein said n is an integer from 11 to 13.

7. A compound selected from the group consisting of glycidic and thioglycidic acid derivatives having the formula:

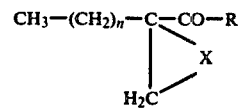

wherein n is an integer from 10 to 15; R is a member selected from the group consisting of OH, O-loweralkyl, $NH_2$, NH-loweralkyl, NH-loweralkyl-OH and N(loweralkyl)$_2$; X is a member selected from the group consisting of O and S; and the therapeutically active basic salts of the foregoing acids.

8. The compounds of claim 7 wherein said n is an integer from 11 to 13.

9. n-Butyl 2-tetradecyl glycidate.
10. Methyl 2-tetradecyl glycidate.
11. Methyl 2-undecylglycidate.
12. Methyl 2-dodecylglycidate.
13. Methyl 2-tridecylglycidate.
14. Methyl 2-tetradecylthioglycidate.
15. 2-Tetradecylglycidic acid.
16. 2-Tetradecylthioglycidic acid.
17. 2-Tetradecylglycidamide.
18. N-Ethyl-2-tetradecylthioglycidamide.
19. Methyl 2-tetradecyl-3-methylglycidate.
20. Methyl 2-tetradecyl-3,3-dimethylglycidate.
21. N,N-Dimethyl-2-tetradecylglycidamide.
22. N-(2-Hydroxyethyl)-2-tetradecylglycidamide.
23. Methyl 2-hexadecylglycidate.
24. A compound selected from the group consisting of glycidic and thioglycidic acid derivatives having the formula:

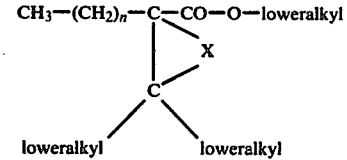

wherein n is an integer from 10 to 15; and X is a member selected from the group consisting of O and S.

25. The compounds of claim 24 wherein said n is an integer from 11 to 13.

* * * * *